(12) United States Patent
Romoscanu

(10) Patent No.: US 11,622,806 B2
(45) Date of Patent: *Apr. 11, 2023

(54) CONTROL HANDLE FOR A CONTACT FORCE ABLATION CATHETER

(71) Applicant: St. Jude Medical International Holding S.à r.l., Luxembourg (LU)

(72) Inventor: Alexandre Ioan Romoscanu, Geneva (CH)

(73) Assignee: St Jude Medical International Holding S.À R.L., Luxembourg (LU)

( * ) Notice: Subject to any disclaimer, the term of this patent is extended or adjusted under 35 U.S.C. 154(b) by 1087 days.

This patent is subject to a terminal disclaimer.

(21) Appl. No.: 16/025,471

(22) Filed: Jul. 2, 2018

(65) Prior Publication Data

US 2019/0000546 A1 Jan. 3, 2019

Related U.S. Application Data

(63) Continuation of application No. 14/562,370, filed on Dec. 5, 2014, now Pat. No. 10,034,706, which is a (Continued)

(51) Int. Cl.
*A61B 18/14* (2006.01)
*A61B 17/00* (2006.01)
(Continued)

(52) U.S. Cl.
CPC .......... *A61B 18/1492* (2013.01); *A61B 34/76* (2016.02); *A61M 25/0136* (2013.01);
(Continued)

(58) Field of Classification Search
CPC ...... A61B 18/1492; A61B 2018/00318; A61B 2017/003; A61B 2017/00318
See application file for complete search history.

(56) References Cited

U.S. PATENT DOCUMENTS 4,836,907 A * 6/1989 Pedersen .............. G01N 27/404
204/415
4,874,371 A 10/1989 Comben et al.
(Continued)

FOREIGN PATENT DOCUMENTS

CN 101927053 B 1/2015
EP 0889744 B1 1/2004
(Continued)

*Primary Examiner* — Eun Hwa Kim
(74) *Attorney, Agent, or Firm* — Kilpatrick Townsend & Stockton LLP

(57) ABSTRACT

A control handle for a steerable catheter body for navigation of the catheter body through a biological lumen and manipulation at a treatment site. The control handle includes a housing assembly that houses a piston assembly and a resistance adjusting assembly. The resistance adjusting assembly can be adjusted to provide the desired frictional characteristics of the user for control of the resistance between the piston assembly and the housing assembly. In one embodiment, the piston assembly is configured to provide a frictional resistance that varies dynamically to substantially match the restorative force across the range of catheter tip deflection. Other embodiments include a vibrating member that provides tactile feedback to the operator to indicate conditions at the distal end of the catheter, such as contact force.

18 Claims, 10 Drawing Sheets

Related U.S. Application Data continuation of application No. 13/084,214, filed on Apr. 11, 2011, now Pat. No. 8,906,013.

(60) Provisional application No. 61/409,379, filed on Nov. 2, 2010, provisional application No. 61/381,643, filed on Sep. 10, 2010, provisional application No. 61/322,670, filed on Apr. 9, 2010.

(51) Int. Cl.
*A61B 34/00* (2016.01)
*A61M 25/01* (2006.01)
*A61B 18/00* (2006.01)

(52) U.S. Cl.
CPC ... *A61M 25/0155* (2013.01); *A61B 2017/003* (2013.01); *A61B 2017/00318* (2013.01); *A61B 2017/00323* (2013.01); *A61B 2017/00331* (2013.01); *A61B 2018/00297* (2013.01); *A61B 2018/00577* (2013.01); *A61B 2018/1407* (2013.01); *A61M 2205/332* (2013.01)

(56) References Cited

U.S. PATENT DOCUMENTS

| | | |
|---|---|---|
| 4,960,134 A | 10/1990 | Webster, Jr. |
| 5,117,839 A | 6/1992 | Dance |
| 5,190,050 A | 3/1993 | Nitzsche |
| 5,224,939 A | 7/1993 | Holman et al. |
| 5,228,441 A | 7/1993 | Lundquist |
| 5,242,430 A | 9/1993 | Arenas et al. |
| 5,315,996 A | 5/1994 | Lundquist |
| 5,318,525 A | 6/1994 | West et al. |
| 5,322,064 A | 6/1994 | Lundquist |
| 5,327,905 A | 7/1994 | Avitall |
| 5,352,197 A | 10/1994 | Hammersmark et al. |
| 5,380,301 A | 1/1995 | Prichard et al. |
| 5,383,852 A | 1/1995 | Stevens-Wright |
| 5,383,923 A | 1/1995 | Webster, Jr. |
| 5,395,327 A | 3/1995 | Lundquist et al. |
| 5,397,304 A | 3/1995 | Truckai |
| 5,400,783 A | 3/1995 | Pomeranz et al. |
| 5,435,805 A * | 7/1995 | Edwards .................. A61N 1/06 604/22 |
| 5,437,664 A | 8/1995 | Cohen |
| 5,441,483 A | 8/1995 | Avitall |
| 5,456,254 A | 10/1995 | Pietroski et al. |
| 5,456,664 A | 10/1995 | Heinzelman et al. |
| 5,462,527 A | 10/1995 | Stevens-Wright et al. |
| 5,545,200 A | 8/1996 | West et al. |
| 5,562,619 A | 10/1996 | Mirarchi et al. |
| 5,611,777 A | 3/1997 | Bowden et al. |
| 5,626,136 A | 5/1997 | Webster, Jr. |
| 5,676,653 A | 10/1997 | Taylor et al. |
| 5,702,433 A | 12/1997 | Taylor et al. |
| 5,715,817 A | 2/1998 | Stevens-Wright et al. |
| 5,715,832 A | 2/1998 | Koblish et al. |
| 5,728,144 A | 3/1998 | Edwards et al. |
| 5,779,669 A | 7/1998 | Haissaguerre et al. |
| 5,791,350 A | 8/1998 | Morton |
| 5,823,955 A | 10/1998 | Kuck et al. |
| 5,827,278 A | 10/1998 | Webster, Jr. |
| 5,861,024 A | 1/1999 | Rashidi |
| 5,865,800 A | 2/1999 | Mirarchi et al. |
| 5,876,373 A | 3/1999 | Giba et al. |
| 5,879,295 A | 3/1999 | Li et al. |
| 5,881,727 A | 3/1999 | Edwards |
| 5,882,333 A | 3/1999 | Schaer et al. |
| 5,897,529 A | 4/1999 | Ponzi |
| 5,904,667 A | 5/1999 | Falwell |
| 5,910,129 A | 6/1999 | Koblish et al. |
| 5,916,214 A | 6/1999 | Cosio et al. |
| 5,931,811 A | 8/1999 | Haissaguerre et al. |
| 5,935,102 A | 8/1999 | Bowden et al. |
| 5,944,690 A | 8/1999 | Falwell et al. |
| 6,013,052 A | 1/2000 | Durman et al. |
| 6,027,473 A | 2/2000 | Ponzi |
| 6,063,098 A * | 5/2000 | Houser ............ A61B 17/22012 606/169 |
| 6,064,905 A | 5/2000 | Webster, Jr. et al. |
| 6,074,379 A | 6/2000 | Prichard |
| 6,096,036 A | 8/2000 | Bowe et al. |
| 6,123,699 A | 9/2000 | Webster, Jr. |
| 6,156,027 A | 12/2000 | West |
| 6,171,277 B1 | 1/2001 | Ponzi |
| 6,183,435 B1 | 2/2001 | Bumbalough et al. |
| 6,183,463 B1 | 2/2001 | Webster, Jr. |
| 6,198,974 B1 | 3/2001 | Webster, Jr. |
| 6,224,587 B1 | 5/2001 | Gibson |
| 6,263,224 B1 | 7/2001 | West |
| 6,267,746 B1 | 7/2001 | Bumbalough |
| 6,270,496 B1 | 8/2001 | Bowe et al. |
| 6,273,404 B1 | 8/2001 | Holman et al. |
| 6,468,260 B1 | 10/2002 | Bumbalough et al. |
| 6,491,681 B1 | 12/2002 | Kunis et al. |
| 6,500,167 B1 | 12/2002 | Webster, Jr. |
| 6,522,933 B2 | 2/2003 | Nguyen |
| 6,533,783 B1 | 3/2003 | Tollner |
| 6,551,302 B1 | 4/2003 | Rosinko |
| 6,554,794 B1 | 4/2003 | Mueller et al. |
| 6,579,279 B1 | 6/2003 | Rabiner et al. |
| 6,602,278 B1 | 8/2003 | Thompson et al. |
| 6,652,506 B2 | 11/2003 | Bowe et al. |
| 6,663,588 B2 | 12/2003 | DuBois et al. |
| 6,679,873 B2 | 1/2004 | Rabiner et al. |
| 6,695,808 B2 | 2/2004 | Tom |
| 6,776,765 B2 | 8/2004 | Soukup et al. |
| 6,783,521 B2 | 8/2004 | Ponzi et al. |
| 6,802,835 B2 | 10/2004 | Rabiner et al. |
| 6,866,662 B2 | 3/2005 | Fuimaono et al. |
| 6,913,594 B2 | 7/2005 | Coleman et al. |
| 6,926,669 B1 | 8/2005 | Stewart et al. |
| 6,995,675 B2 | 2/2006 | Curkendall |
| 7,004,937 B2 | 2/2006 | Lentz et al. |
| 7,008,401 B2 | 3/2006 | Thompson et al. |
| 7,081,114 B2 | 7/2006 | Rashidi |
| 7,211,063 B2 | 5/2007 | Tom |
| 7,214,220 B2 | 5/2007 | McGlinch et al. |
| 7,217,256 B2 | 5/2007 | Di Palma |
| 7,285,108 B2 | 10/2007 | Koerner et al. |
| 7,331,958 B2 | 2/2008 | Falwell et al. |
| 7,344,543 B2 | 3/2008 | Sra |
| 7,371,232 B2 | 5/2008 | Scheib |
| 7,371,237 B2 | 5/2008 | Hutchins et al. |
| 7,377,906 B2 | 5/2008 | Selkee |
| 7,387,630 B2 | 6/2008 | Mest |
| 7,524,301 B2 | 4/2009 | Dubois et al. |
| 7,608,063 B2 | 10/2009 | Le et al. |
| 7,625,365 B2 | 12/2009 | McGlinch et al. |
| 7,666,204 B2 | 2/2010 | Thornton et al. |
| 7,691,095 B2 | 4/2010 | Bednarek et al. |
| 7,959,601 B2 | 6/2011 | McDaniel et al. |
| 7,985,215 B2 | 7/2011 | Guo et al. |
| 8,103,327 B2 | 1/2012 | Harlev et al. |
| 8,221,390 B2 | 7/2012 | Pal et al. |
| 8,257,344 B2 | 9/2012 | Ponzi et al. |
| 8,273,016 B2 | 9/2012 | O'sullivan |
| 8,376,990 B2 | 2/2013 | Ponzi et al. |
| 8,447,377 B2 | 5/2013 | Harlev et al. |
| 8,608,703 B2 | 12/2013 | Riles et al. |
| 8,700,120 B2 | 4/2014 | Koblish |
| 8,706,193 B2 | 4/2014 | Govari et al. |
| 8,755,861 B2 | 6/2014 | Harlev et al. |
| 8,777,929 B2 | 7/2014 | Schneider et al. |
| 8,814,824 B2 | 8/2014 | Kauphusman et al. |
| 8,882,705 B2 | 11/2014 | McDaniel et al. |
| 8,996,091 B2 | 3/2015 | de la Rama et al. |
| 9,017,308 B2 | 4/2015 | Klisch et al. |
| 9,101,733 B2 | 8/2015 | McDaniel |
| 9,247,990 B2 | 2/2016 | Kauphusman et al. |
| 9,326,815 B2 | 5/2016 | Watson |
| 9,339,631 B2 | 5/2016 | Graham et al. |
| 9,433,751 B2 | 9/2016 | Ponzi et al. |

(56) References Cited

U.S. PATENT DOCUMENTS

| | | | |
|---|---|---|---|
| 9,468,495 B2 | 10/2016 | Kunis et al. |
| 9,694,159 B2 | 7/2017 | Schneider et al. |
| 10,034,637 B2 | 7/2018 | Harlev et al. |
| 10,052,457 B2 | 8/2018 | Nguyen et al. |
| 10,099,036 B2 | 10/2018 | Heideman et al. |
| 10,898,685 B2 | 1/2021 | Tegg |
| 11,272,886 B2 | 3/2022 | Harlev et al. |
| 2002/0065485 A1 | 5/2002 | DuBois et al. |
| 2002/0165484 A1 | 11/2002 | Bowe et al. |
| 2003/0004506 A1 | 1/2003 | Messing |
| 2005/0038412 A1 | 2/2005 | Rabiner et al. |
| 2005/0219206 A1 | 10/2005 | Schena |
| 2006/0200049 A1 | 9/2006 | Leo |
| 2007/0060847 A1 | 3/2007 | Leo |
| 2007/0088218 A1 | 4/2007 | Mcintyre |
| 2007/0142749 A1 | 6/2007 | Khatib et al. |
| 2008/0009750 A1 | 1/2008 | Aeby et al. |
| 2008/0294144 A1 | 11/2008 | Leo |
| 2009/0054804 A1 | 2/2009 | Gharib et al. |
| 2009/0177095 A1 | 2/2009 | Gharib et al. |
| 2009/0287092 A1 | 11/2009 | Leo |
| 2009/0287188 A1 | 11/2009 | Golden et al. |
| 2010/0073150 A1 | 3/2010 | Olson et al. |
| 2011/0251519 A1 | 10/2011 | Romoscanu |
| 2016/0213423 A1 | 7/2016 | Kauphusman et al. |

FOREIGN PATENT DOCUMENTS

| | | |
|---|---|---|
| EP | 1254641 B1 | 11/2008 |
| EP | 1690564 B1 | 4/2009 |
| EP | 1723981 B1 | 8/2010 |
| EP | 2135634 B1 | 10/2011 |
| EP | 2018203 B1 | 6/2012 |
| EP | 1814450 B1 | 1/2013 |
| EP | 2269532 B1 | 3/2013 |
| EP | 2915555 A1 | 9/2015 |
| EP | 1968679 B1 | 9/2016 |
| EP | 2241279 B1 | 9/2016 |
| EP | 1759668 B1 | 12/2018 |
| EP | 2234537 B1 | 1/2019 |
| EP | 2550989 B1 | 6/2019 |
| EP | 2155301 B1 | 4/2021 |
| JP | 4545384 B2 | 7/2010 |
| JP | 4887810 B2 | 2/2012 |
| JP | 5154031 B2 | 2/2013 |
| JP | 5193190 B2 | 5/2013 |
| JP | 5372314 B2 | 12/2013 |
| JP | 2014014713 A | 1/2014 |
| JP | 5762697 B2 | 6/2015 |
| JP | 5944331 B2 | 7/2016 |
| WO | 9843530 A1 | 10/1998 |
| WO | 0168178 A1 | 9/2001 |
| WO | 2007015139 A2 | 2/2007 |
| WO | 2008091197 A1 | 7/2008 |

* cited by examiner

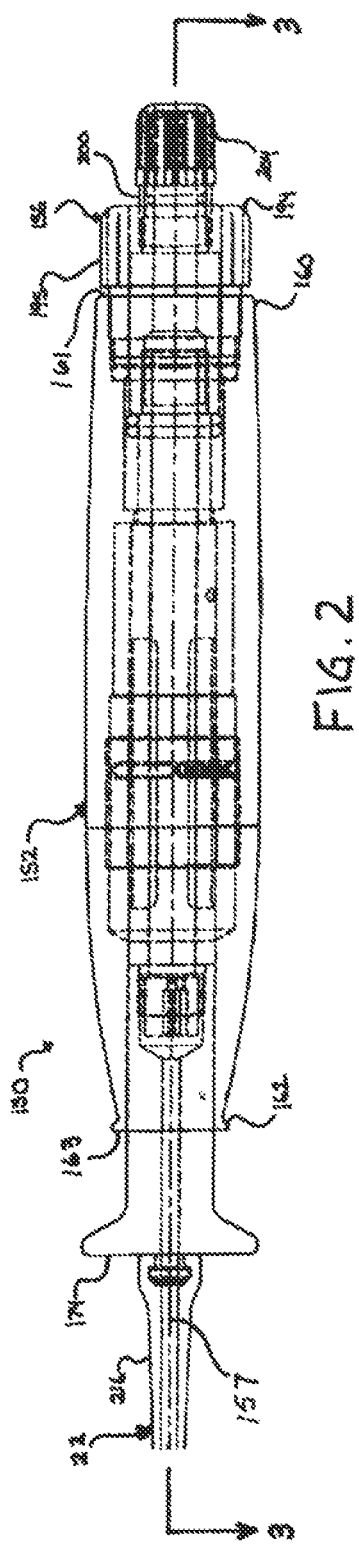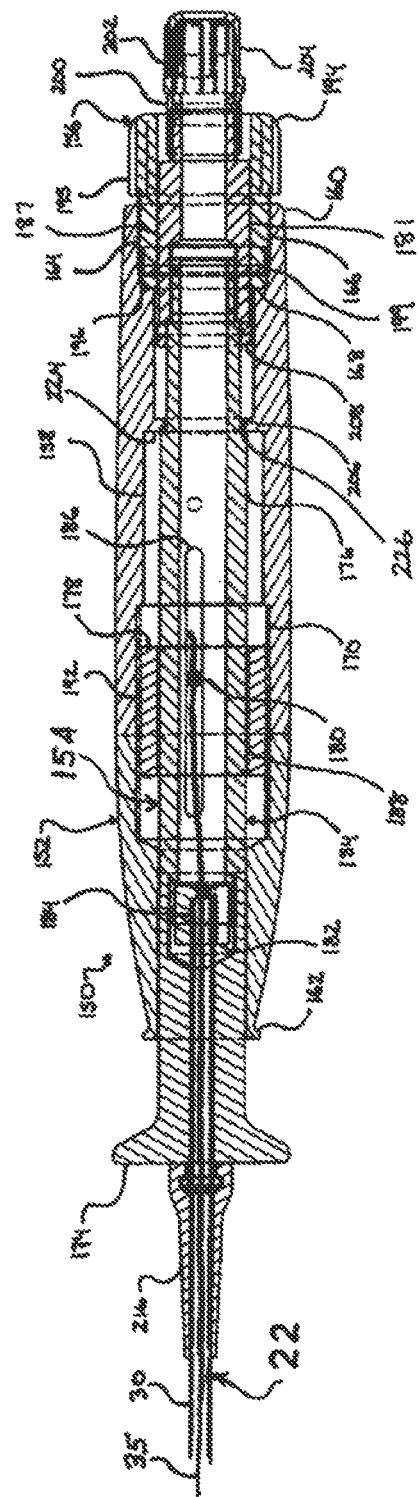

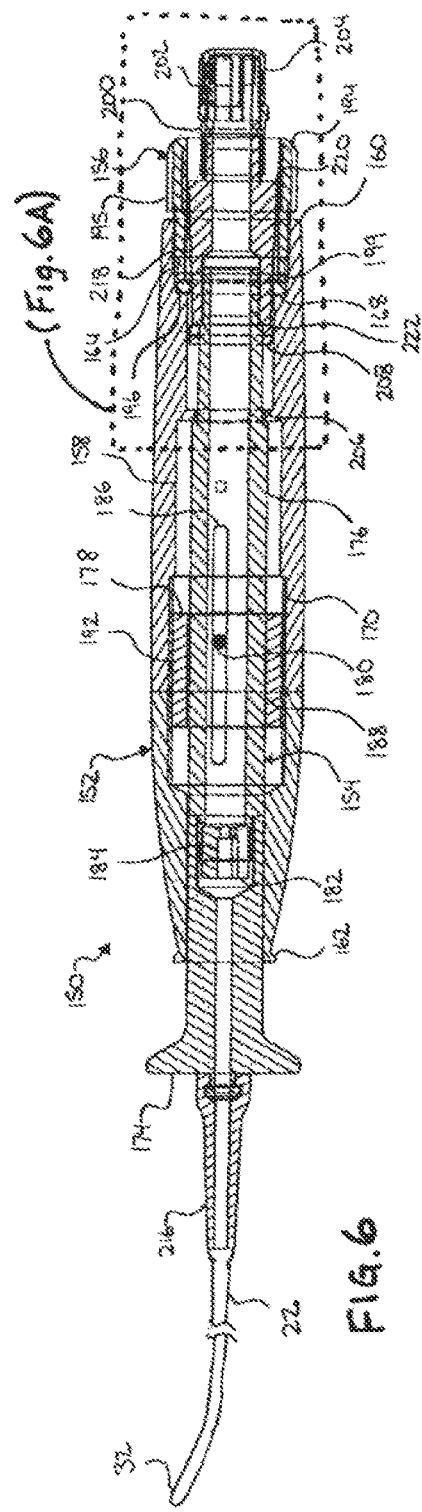

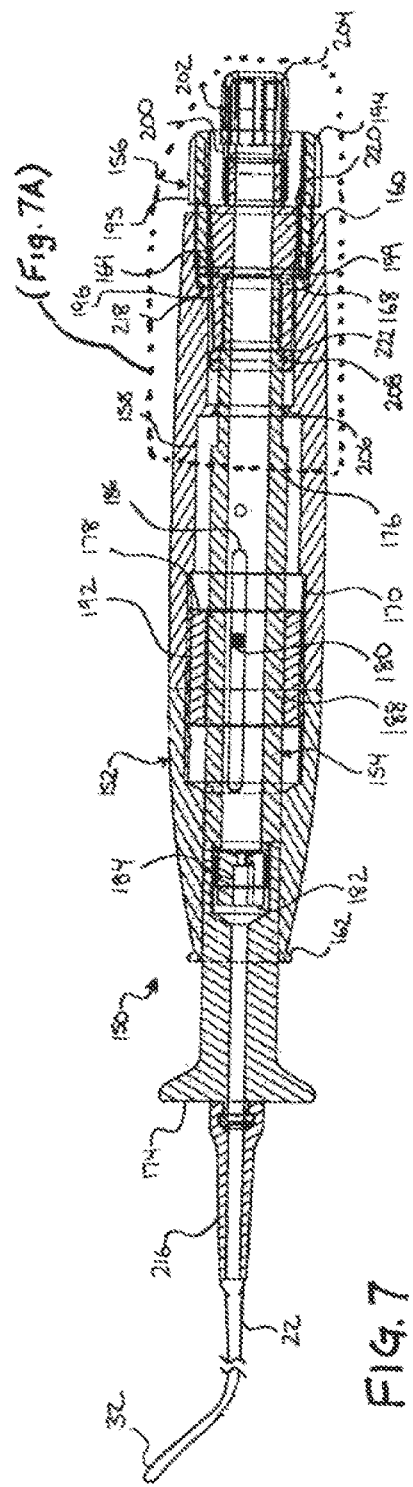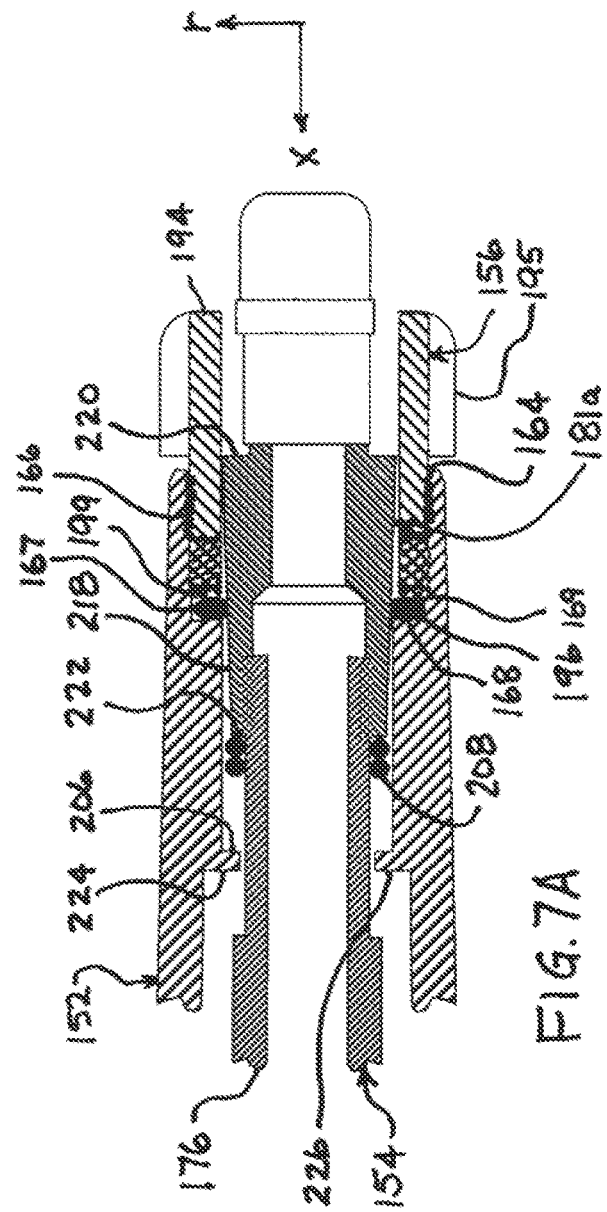

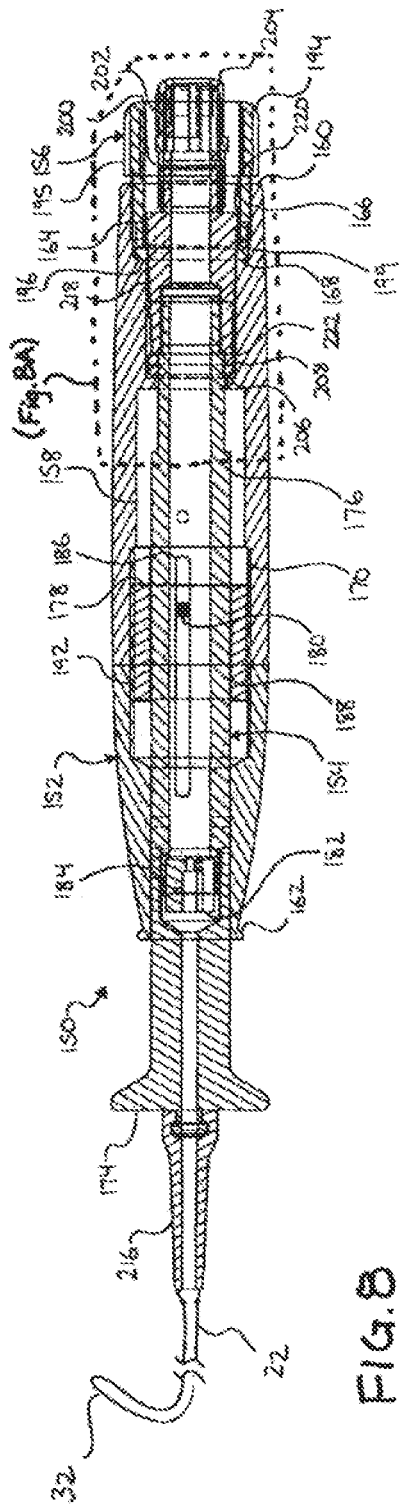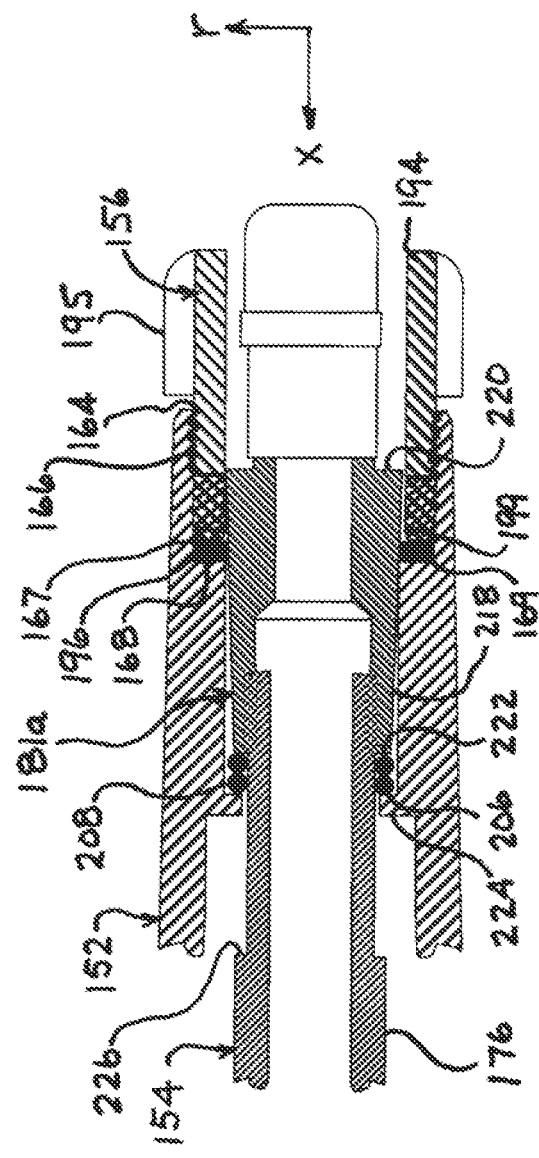

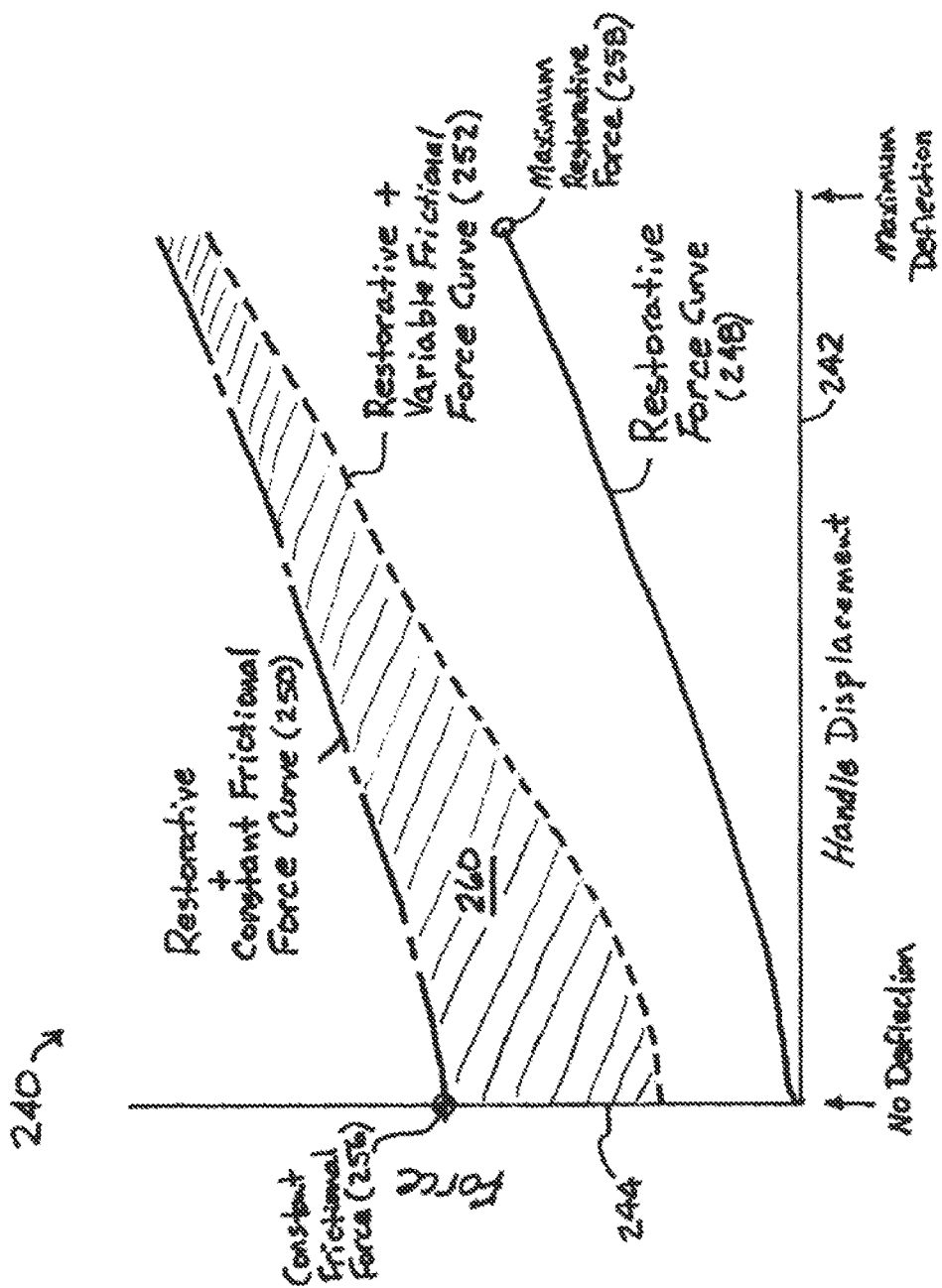

CONTROL HANDLE FOR A CONTACT FORCE ABLATION CATHETER

CROSS-REFERENCE TO RELATED APPLICATIONS

This application is a continuation application of U.S. patent application Ser. No. 14/562,370, filed 5 Dec. 2014, now U.S. Pat. No. 10,034,706, issued 31 Jul. 2018 (the '370 application); which is a continuation application of U.S. patent application Ser. No. 13/084,214, filed 11 Apr. 2011, now U.S. Pat. No. 8,906,013, issued 9 Dec. 2014 (the '214 application). This application claims the benefit of U.S. Provisional Patent Application No. 61/322,670 (the '670 application), filed 9 Apr. 2010; U.S. Provisional Patent Application No. 61/381,643, filed 10 Sep. 2010 (the '643 application); and U.S. Provisional Patent Application No. 61/409,379, filed 2 Nov. 2010 (the '379 application). The '370 application; the '214 application; the '670 application; the '643 application; and the '379 application are hereby incorporated by reference as though fully set forth herein.

FIELD OF THE DISCLOSURE

The invention is generally directed to a steerable ablation catheter system with a deflectable tip. More specifically, the invention is directed to a control handle adapted to control the deflection of a steering spine within a patient's body.

BACKGROUND OF THE DISCLOSURE

Catheter ablation is a surgical procedure in which a catheter having an ablation tip is fed through various biological lumens to reach targeted tissue within the body. Radiofrequency current ("RF current") is transmitted through electrodes disposed within the biological lumen and emitted from the ablation tip into the targeted tissue. The ablation tip is placed in close proximity to or in contact with the targeted tissue to maximize the amount of RF current supplied directly to the targeted tissue and limit the amount of untargeted tissue exposed to the RF current. Because the ablation catheter is navigated through existing biological lumen to reach the targeted tissue, catheter ablation surgery is less invasive than other available surgical techniques for reaching the targeted tissue, such as open heart surgery.

However, biological lumens and particularly blood vessels are often circuitous in nature and typically intersect many other biological lumens, presenting challenges with respect to catheter navigation therethrough. In order to reach the targeted tissue, the ablation tip must be threaded through the bends in the biological lumen and through the various intersections to reach the targeted tissue. Once near the target tissue, the operator must be able to accurately position the tip of the catheter for adequate delivery of the ablation energy. The difficult navigation process required can extend the surgical time considerably and can result in injury to the patient.

Catheter bodies often comprise an internal pull wire for deflecting the tip of the catheter body to more easily navigate the various turns and bends of the biological lumen. The pull wire is typically affixed proximate the tip of the catheter body and extends through the catheter body exiting the end of the catheter body that remains outside the patient's body. An operator can apply a pulling force to the pull wire to cause the tip of the catheter to deflect. Handles are often affixed to the proximal end of the catheter body to manipulate the pull wire for control of the defection of the catheter.

However, different operators often have different tactile preferences as to the amount of force required to deflect the tip of the catheter a given amount. A standardized or factory set force-to-deflection relationship may cause some operators to over-deflect the catheter tip (thus denying the operator resolution in deflecting the tip), while causing others discomfort because the force requirement for a given tip deflection is uncomfortably high.

One steering mechanism used for deflection of a catheter tip is the so-called "steering spine." Steering spines are characterized by a continuous portion (i.e. the "spine") that extends from the proximal to the distal end of the steering mechanism. An advantage of the steering spine is that the resilience or elasticity of the continuous spine portion generates its own restorative force when the spine is deflected from its at-rest position, thus negating the need for a second pull wire to restore the tip to a straightened geometry.

The restorative force exerted on the pull wire by a steering spine typically depends on the nominal deflective position of the steering spine. That is, the restorative force exerted by the steering spine can be substantially less when the steering spine is near a slack or neutral (un-deflected) orientation than when the steering spine is nearly fully deflected. For the frictional force to counter the restorative force across the range of tip deflection, the frictional force needs to be set high enough to counter the steering spine at the maximum restorative force (i.e. at the maximum tip deflection). Meanwhile, the operator typically spends most of the time with the tip at or near the neutral orientation. Thus, the operator has to overcome a high frictional force when the tip is proximate the neutral orientation, which can lead to operator fatigue and poor positional resolution.

Operating rooms can be the host to a plethora of sounds. At any given time during a surgical procedure, several instruments can be emitting audio sounds in vying for the attention of attending personnel. Catheter systems that utilize sound to alert an operator can, in some instances, lose effectiveness as being yet another sound among the cacophony.

A device that can accommodate the tactile preferences of an individual operator in the control of catheter tip deflection would be welcome. A frictional device that can substantially match the varying restorative force of the steering spine across the range of tip deflection while reducing the force requirements at low tip deflections would also be welcome. A catheter system that implements non-auditory sensory perceptions would also find utility in the modern operating room.

SUMMARY OF THE DISCLOSURE

Various embodiments of the invention are directed to better control of tip deflection for catheters that utilize a steering spine for control of tip deflection. Typically, the restorative force of a steering spine is opposed at least in part by components that generate a frictional force within the steering handle. Certain embodiments of the invention provide an adjustable friction mechanism within the handle allowing an operator to adjust and attain a balance between the restorative and frictional forces suitable to the individual operator to provide a desired actuation force magnitude to overcome this balance.

Other embodiments provide a frictional force that varies dynamically with the restorative force of the steering spine across the range of tip deflection. Certain embodiments of the invention provide for variable friction across the range of deflection of the steering spine without need for manually adjusting the friction at each nominal deflection position. The variable friction enables the counterbalancing frictional force to change with and substantially match the restorative force across the deflection range of the steering spine.

The control handle according to an embodiment of the invention is adapted to apply an adjustable frictional force as a counterbalance to the restorative force. The applied frictional force (and subsequent steady state force) can be adjusted manually by an operator according to the operator's tactile preference. The frictional force can be adjusted so that the balance requires an operator to apply a pull force to increase the deflection of the steerable tip and a pushing force to decrease the deflection of the steerable tip. Also, in one embodiment, the frictional force mechanism can be configured so that the frictional force substantially equals the restorative force across the deflective range of the steerable tip.

Structurally, the control handle can comprise a housing assembly and a piston assembly. The housing assembly includes a guide for centering the piston assembly. The piston assembly further comprises a central slider adapted to slide axially relative to the guide. The guide is adapted to receive the proximal extremity of the pull wire such that sliding the housing assembly relative to the central slider applies a pull force to the pull wire to defect the steerable tip. The central slider can further comprise a steering knob adapted to allow an operator to hold the central slider in place while sliding the housing assembly to apply a pull force to the pull wire.

The control handle can further comprise a resistance adjusting assembly adapted to apply a frictional force that resists the piston assembly. In one embodiment, the resistance adjusting assembly comprises a knob and a deformable o-ring or gasket. The piston assembly further comprises an exterior glide surface operatively coupled with the central slider that slidably engages the deformable gasket. Tightening the knob applies a deforming force to the deformable gasket causing the gasket to constrict inward against the glide surface of the piston assembly thereby manually increasing the friction between the piston assembly and the housing assembly to dampen the movement of the central slider and provide a counteracting frictional force to the restorative force.

According to an embodiment of the invention, the glide surface can be angled or tapered relative to the central axis of the slider such that the clearance between the housing assembly and the glide surface changes at the point or line of contact between the deformable gasket and the glide surface as the piston assembly is translated in an axial direction. The changing clearance in turn alters the compression of the o-ring or gasket, thereby changing the friction between the central slider and the housing assembly. The dynamically changing frictional force that varies with the position of the central slider allows the control handle to maintain the deflection of the steerable tip at any deflection while closely matching the restorative force of the steering spine, thus requiring less frictional force that needs to be overcome when operating near the neutral orientation.

According to an embodiment of the invention, the handle can further comprise a tactile feedback device for providing a physical sensation to the user corresponding to the force applied to the tip of the catheter system. The tactile feedback device can provide a tactile stimulus, such as a vibration, that varies in a characteristic (e.g., intensity, amplitude or frequency) and in relation to an operating condition experienced at the end effector of the catheter (e.g., contact force, ablation intensity or duration, force-time integration). The characteristic of the tactile stimulus can range from a low or intermittent characteristic when the operating condition initially crosses some threshold to an increasingly pronounced characteristic as the operating condition reaches or exceeds a desired state or enters an excessive state. According to an embodiment of the invention, the tactile feedback device can comprise a vibrating motor to provide a tactile vibrating sensation. The feedback device can additionally comprise an auditory device providing an audible physical sensation.

The above summary of the various representative embodiments of the invention is not intended to describe each illustrated embodiment or every implementation of the invention. Rather, the embodiments are chosen and described so that others skilled in the art can appreciate and understand the principles and practices of the invention. The figures in the detailed description that follow more particularly exemplify these embodiments.

BRIEF DESCRIPTION OF THE FIGURES

FIG. 2 is a plan view of a control handle according to an embodiment of the invention;

FIG. 3 is a sectional side view of the control handle of FIG. 2;

FIG. 6 is a representative view of a catheter at or near a neutral orientation of a steerable tip according to an embodiment of the invention;

FIG. 6A is an enlarged partial sectional side view of the control handle in the orientation of FIG. 6;

FIG. 7 is a representative view of a catheter in an intermediate flexed orientation of a steerable tip according to an embodiment of the invention;

FIG. 7A is an enlarged partial sectional side view of the control handle in the orientation of FIG. 7;

FIG. 8 is a representative view of a catheter in a fully flexed orientation of a steerable tip according to an embodiment of the invention;

FIG. 8A is an enlarged partial sectional side view of the control handle in the orientation of FIG. 8;

FIG. 9 is a graph of the forces of operation of various embodiments of the invention.

DETAILED DESCRIPTION OF THE FIGURES

Figure 1:
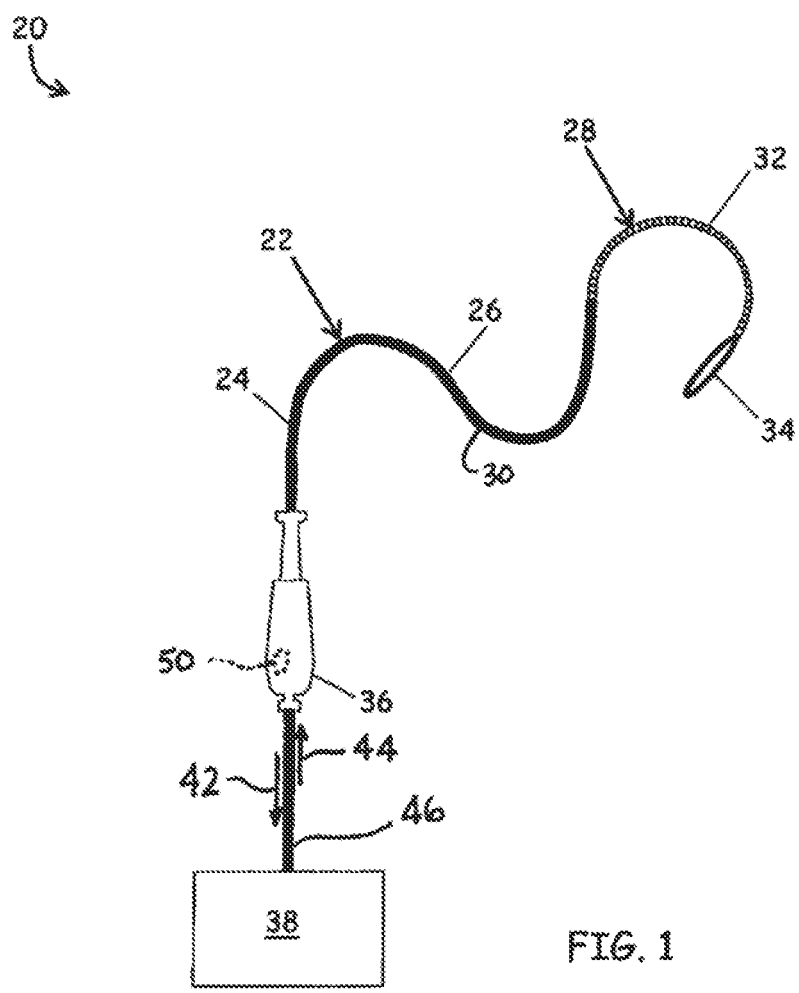
FIG. 1 is a schematic of the components of a catheter system according to an embodiment of the invention.

Referring to FIG. 1, a catheter system 20 is depicted in an embodiment of the invention. The catheter system 20 comprises an elongated catheter assembly 22 having a proximal portion 24, a middle portion 26 and a distal portion 28. A catheter shaft 30 defines the outer radial surface of catheter assembly 22. The distal portion of catheter assembly 22 includes a steering section 32 and an end effector 34. Catheter system 20 can be equipped with instrumentation for determination of at least one operating condition of catheter assembly 22 (e.g., temperature, contact force, contact impedance, irrigation flow). In some embodiments, the instrumentation is disposed in end effector 34. Steering section 32 further comprises a pull wire 35 (depicted in FIG. 3) disposed within elongated catheter assembly 22 and affixed to the distal end of steering section 32, wherein apply a pulling force to the pull wire causes steering section 32 to deflect. In one embodiment, the steering section 32 comprises a steering spine (not depicted). In one embodiment, proximal portion 24 is operatively coupled with a control handle 36.

Control handle 36 may be operatively coupled with a controller 38 containing various appurtenances that augment the operation of the catheter system 20. Non-limiting examples of the appurtenances of controller 38 include power sources and/or irrigation systems for sourcing the end effector 34, optical sources for sourcing fiber optic systems within the catheter system 20, data acquisition devices for monitoring instrumentation of the catheter system 20, and/or control systems for controlling the sourcing of the end effector 34. Controller 38 can be configured to receive an input signal or signals 42 from catheter assembly 22 and to produce an output signal or signals 44 to catheter assembly 22. Controller 38 can be coupled to control handle 36 and catheter assembly 22 via a cable 46. Cable 46 can contain instrumentation leads, power source leads, irrigation lines and/or fiber optics. In some instances, certain input signal(s) 42 and output signal(s) 44 are transmitted wirelessly (i.e. without being routed through cable 46), such as by radio transmitter and receiver.

In certain embodiments, a tactile feedback device 50 is operatively coupled to control handle 36. Tactile feedback device 50 can be any of a variety of devices that produce tactile stimulus, such as vibration, electrical impulses or temperature change. According to an embodiment of the invention, an auditory speaker (not depicted) for providing an audible sound can also be provided.

In operation, the instrumentation of catheter assembly 22 detects at least one operating condition of catheter assembly 22, and sends input signal 42 to controller 38. Examples of operating parameters upon which the operating condition can be predicated includes a force, a temperature, a timer that provides a duration or delay, and/or an irrigation flow. Some of these parameters can be sensed by input signal 42 to controller 38; others can be commensurate with the operation of a component within controller 38, thus requiring no input signal per se.

In some embodiments, controller 38 receives input signal 42 and is configured to send output signal 44 to tactile feedback device 50 if input signal 42 corresponds to a known or predetermined condition regarding the operation of catheter assembly 22. Output signal 44, when present, causes tactile feedback device 50 to generate a tactile stimulus in or on control handle 36 that is sensed by the operator.

For example, in some embodiments, the instrumentation can include a force sensing assembly contained within or operatively coupled with end effector 34 for detection of contact force between an organ or vessel and end effector 34. Non-limiting examples of force sensing assemblies are disclosed at U.S. Patent Application Publication Nos. 2006/200049, 2007/060847, 2008/0294144, 2009/287092, 2009/177095 to Leo et al. and U.S. Patent Application Publication No. 2008/009750 to Aeby et al., all of which are assigned to assignee of this application, and the disclosures of which are hereby incorporated by reference in their entirety herein except for express definitions contained therein. For such an embodiment, controller 38 can be configured to accept input signal or signals 42 from the force sensor, and to produce output signal 44 to tactile feedback device 50 if input signal(s) 42 from the force sensor correspond to a contact force that exceeds a certain magnitude or falls within a certain range of magnitudes. Tactile feedback device 50 will then produce a tactile stimulus (e.g., a vibration), telling the operator that the contact force is over a certain threshold or within a certain range.

In another example, end effector 34 can be fitted with an ablation head and controller 38 equipped with an energy source. In this embodiment, controller 38 could be configured to send output signal 44 to tactile feedback device 50 only when the ablation head is energized. It is noted that controller 38 can be configured generate output signal 44 concurrently with energization of the ablation head, and as such does not receive an input signal.

In addition, controller 38 can be configured to produce output signal 44 and subsequent tactile stimulus to have certain characteristics that depend on the relative state or magnitude of the operating condition. Returning to the example of contact force, and by way of further example, controller 38 can be configured to output a steady output signal 44 when input signal(s) 42 correspond to a contact force that is within a desired range of operation, and to output an intermittent output signal 44 when input signal(s) 42 correspond to a contact force that exceeds the desired range of operation. For a configuration wherein tactile feedback device 50 is a vibrating motor, the operator would know that a steady vibration is an indication that the contact force is at the desired level, and that an intermittent vibration is an indication that the contact force is too great. Other characteristics can also be implemented by proper manipulation of output signal 44, such as steady but increasing vibration as the contact force is increased through desired range, changing to a pulsed vibration when exceeding the desired force range.

Another characteristic of tactile stimulus is vibration frequency. Tactile feedback device 50 could be configured to output a varying vibration frequency that varies with, for example, a voltage level of output signal 44 from controller 38. Or tactile feedback device 50 could comprise two vibrating motors, each producing a different vibration frequency. With these arrangements, controller 38 and tactile feedback device 50 could be configured to produce vibration frequencies that indicate the various magnitudes of the contact force. The changing frequencies of vibration can also produce an auditory stimulus, providing the operator with further sensory capability.

In some embodiments, controller 38 can include analog electronic components to execute the control logic required to monitor input signal(s) 42 and produce output signal 44 when certain predetermined conditions of operation are met. In other embodiments, controller 38 comprises digital components such as a microprocessor that accesses programmed instructions from a digital memory device, wherein the instructions can comprise the steps of receiving input signal (s) 42, determining whether catheter assembly 22 is in a predetermined condition of operation, and sending output signal 44 to tactile feedback device 50. In still other embodiments, controller 38 is includes both analog and digital components. Controller 38 can comprise a general purpose computer, or a specialized console configured for operation only with catheter system 20.

Figure 4:
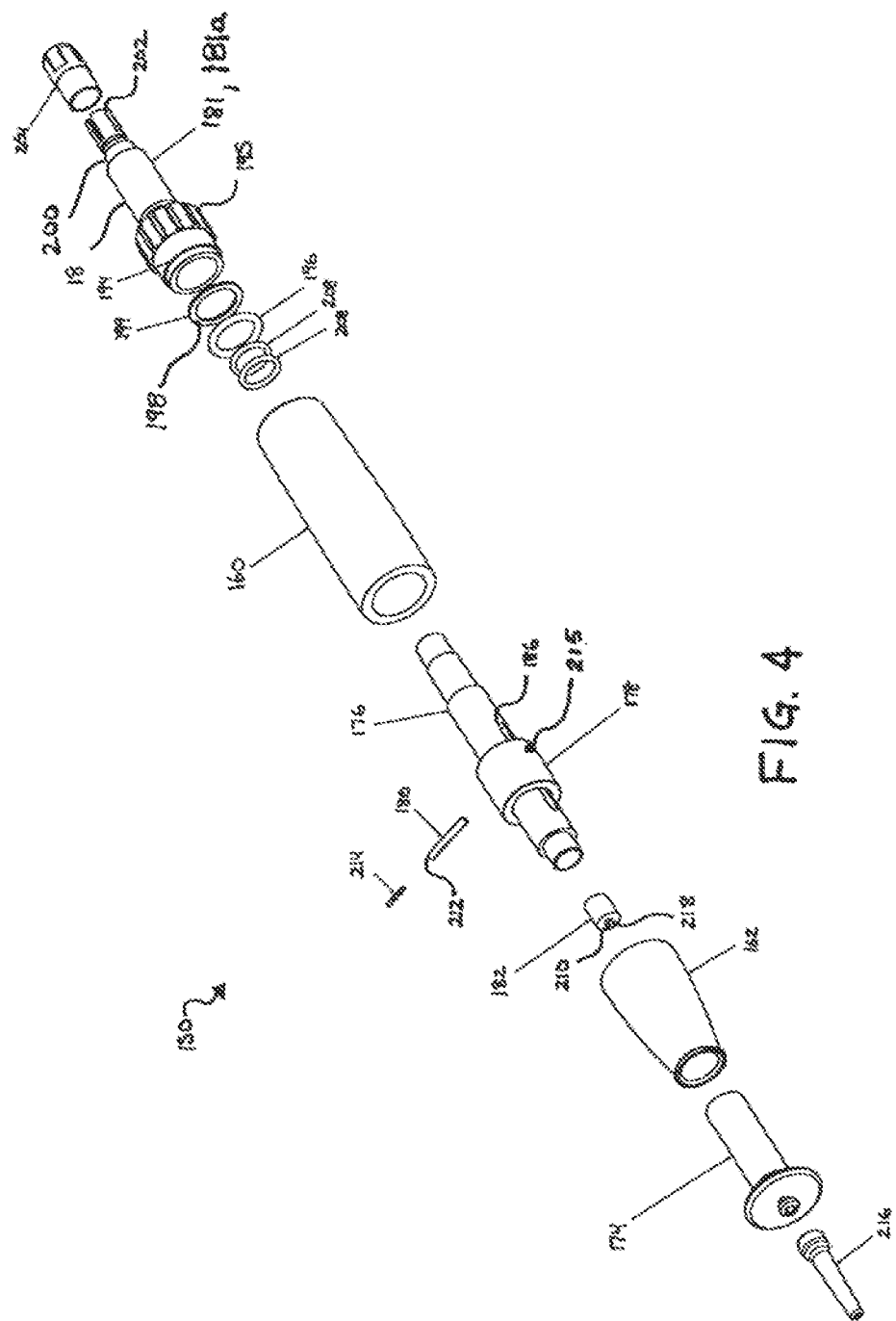
FIG. 4 is an exploded perspective view of a control handle of FIG. 2.

Referring to FIGS. 2 through 4, a control handle 150 is depicted in an embodiment of the invention. Control handle 150 comprises a housing assembly 152, a steering or piston assembly 154 and a resistance adjusting assembly 156, all concentric about a central axis 157. Piston assembly 154 can comprise a steering knob 174, a central slider 176 and a glide assembly 181. In various embodiments, piston assembly 154 includes at least one notch or slot 186 that extends axially along a portion of central slider 176. Piston assembly 154 also includes a lock or transition piece 182 defining a seat lumen or cavity 184. In one embodiment, transition piece is disposed in the proximal end of steering knob 174 and glued into place. Piston assembly 154 also includes a glide surface 187 defined by the exterior of the glide assembly 181. Steering knob 174 is affixed to or is integral with central slider 176 and adapted to allow a user to hold or change the position of central slider 176 within housing assembly 152.

Housing assembly 152 includes a proximal portion 160 having a proximal end 161 and a distal portion 162 having a distal end 163. Housing assembly 152 also defines a housing lumen or central bore 158 concentric about central axis 157. Central bore 158 can further comprise a threaded portion 170 adapted to adjustably engage a slider housing or piston guide 178 adapted to receive a portion of piston assembly 154. Piston guide 178 includes a smooth bore 188 adapted to slidably receive central slider 176 and can further include a threaded exterior 192 for adjustable engagement with threaded portion 170 of central bore 158. Piston guide 178 can be coupled with a split pin 180 that extends into or across the piston guide 178 and into or through the slot 186 of the central slider 176. Split pin 180, when implemented, can further comprise a pull wire notch 212 and a pull wire crimp 214 for capturing the proximal end of pull wire 35. In one embodiment, piston guide 178 includes access holes 215 for mounting split pin 180. Proximal portion 160 can further comprise a port 164 having a threaded portion 166 adapted to operably engage resistance adjusting assembly 156 and also can comprise a radial step 167 that defines a shoulder 168 at the base of port 164. In one embodiment, shoulder 168 cooperates with a bearing face 198 of resistance adjusting assembly 156 to define a gland 169. In one embodiment, a deformable gasket 196, such as an o-ring, is disposed in gland 169. The gland 169 can be continuous.

In some embodiments, resistance adjusting assembly 156 comprises a threaded member 194 and a bushing 199. Threaded member 194 is adapted to adjustably engage threaded portion 166 of port 164. Gland 169 defines a volume that can be varied with the position of bushing 199 and/or threaded member 194. In some embodiments, bushing 199 is a washer, as depicted in FIG. 4.

Threaded member 194 can further comprise a grip 195 adapted to assist users in rotating threaded member 194. Bushing 199, when implemented, is disposed between threaded member 194 and deformable gasket 196 to define bearing surface 198.

Functionally, threaded member 194 applies a compressive force against deformable gasket 196 causing deformable gasket 196 to deform radially against glide surface 187 of glide assembly 181, thereby providing friction between glide assembly 181 and deformable gasket 196. The friction creates resistance between the piston assembly 154 and housing assembly 152, and can provide better control in manipulation of piston guide 178 and in the amount of tension force on the pull wire. Bushing 199 prevents rotational forces caused by the tightening of threaded member 194 from twisting or damaging deformable gasket 196.

In some embodiments, elongated catheter assembly 22 extends through steering knob 174, with catheter shaft 30 terminating within transition piece 182. Pull wire 35 can extend proximally through transition piece 182 and is coupled to split pin 180. Transition piece 182 can include a slot that extends along one side and enables instrumentation leads that extend from catheter assembly 22 to be routed laterally away from central axis 157. By this arrangement, all of the components of catheter assembly 22 ride along with piston assembly 154, except for pull wire 35 which rides along with housing assembly 152, so that relative movement between piston assembly 154 and housing assembly 152 causes pull wire 35 to be longitudinally displaced relative catheter assembly 22.

Piston assembly 154 can further comprise a chuck 200 affixed to central slider 176 and adapted to receive cable 46 from controller 38. Chuck 200 includes a plurality of locking arms 202 and a compression fitting 204. Once cable 46 is in place within locking arms 202, compressing fitting 204 is slid over plurality of locking arms 202 closing locking arms 202 over a portion of cable 46 to lock in place. In one embodiment of the invention, deformable gasket 196 of resistance adjusting assembly 156 is deformed against chuck 200 to create friction between central slider 176 and housing assembly 152.

In operation, an operator pushes or pulls the piston assembly 154 so that it translates axially relative to the housing assembly 152 between a first position and a second position. This motion also causes glide assembly 181 to translate relative to housing assembly 152 and to cause split pin 180 to slide relative to slot 186 of central slider 176. Translation of split pin 180 also translates pull wire 35 within catheter assembly 22. Pull wire 35 is maintained in a tension state over at least part of the range of motion of split pin 180 with slot 186, the tension being caused by the position of split pin 180 within slot 186 and the restorative force of steering section 32. Translation of piston assembly 154 in the distal direction relative to housing assembly 152 acts to increase the deflection of steering section 32 and increase the tension force on pull wire 35. In contrast, translation of piston assembly 154 in the proximal direction relative to housing assembly 152 acts to reduce the deflection of steering section 32 and decrease the tension of pull wire 35. The catheter system 20 is generally configured so that at some point, the position of the piston assembly 154 relative to the housing assembly 152 causes steering section 32 to return to a relaxed position, depending on the resilience of steering section 32.

Referring specifically to FIG. 3, housing assembly 152 can further comprise a first shoulder 206 adapted to stop glide assembly 181. First shoulder 206 limits the distance piston assembly 154 can travel in a distal direction relative to housing assembly 152. Housing assembly 152 can also comprise a second shoulder 224 opposite first shoulder 206 for engaging an opposing shoulder 226 formed on central slider 176. Second shoulder 224 engages opposing shoulder 226 to limit the distance piston assembly 154 can travel in a proximal direction relative to housing assembly 152. In one embodiment of the invention, housing assembly 152 further comprises at least one cushioning or spacer gasket 208 (two depicted in FIG. 3) disposed between glide assembly 181 and shoulder 206. Spacer gasket(s) 208 can comprise a rubber or synthetic rubber o-ring. Central slider 176 and/or glide assembly 181 can be adapted to maintain the position of spacer gasket(s) 208 along central slider 176 between glide assembly 181 and housing assembly 152.

Functionally, limiting the travel distance of piston assembly 154 within housing assembly 152 can prevent overextension of pull wire 35, as well as excessive slack in pull wire 35. Spacer gasket(s) 208 can further limit the travel distance of piston assembly 154 within housing assembly 152, as well as preventing damage to housing assembly 152 or piston assembly 154.

In some embodiments, proximal portion 24 of elongated catheter assembly 22 passes through a flexible stress reliever 216 attached to the distal end of distal portion 162 to prevent excessive bending at the junction between handle 150 and elongated catheter assembly 22. Optionally, stress reliever 216 can be integral with proximal portion 24.

Transition piece 182 can further comprise a notch 218 through the exterior of transition piece 182 into cavity 184. Notch 218 enables electrodes disposed within elongated catheter assembly 22 to pass through transition piece 182 and to controller 38 powering the electrodes. Transition piece 182 can also further comprise a safety lumen 210 adapted to receive a thread (Kevlar; not depicted) disposed within elongated catheter assembly 22. Safety lumen 210 allows users to retrieve a broken or severed elongated catheter assembly from the body of a patient by pulling on the safety thread.

Referring to FIGS. 5-8, a tapered glide assembly 181a is depicted according to an embodiment of the invention. Tapered glide assembly 181a comprises frustum an angled glide surface 218 having a proximal edge 220 and a distal edge 222. Angled glide surface 218 is tapered radially inward from proximal edge 220 to distal edge 222 such that the outer diameter of tapered glide assembly 181a is narrower at distal edge 222 than proximal edge 220.

In operation, as depicted in FIGS. 6-8 and 6A-8A, angled glide surface 218 varies the radial distance between tapered glide assembly 181a and gland 169 at the location of deformable gasket 196 as central slider 176 is axially translated. Translation of piston assembly 154 in a distal direction (i.e. forward) relative to housing assembly 152 increases the deflection of steering section 32, which increases the restorative force exerted on pull wire 35. Correspondingly, forward translation of piston assembly 154 also decreases the radial distance between tapered guide assembly 181a and gland 169. When deformable gasket 169 is in contact with tapered guide assembly 181a, the reduction in radial distance increases the compression of deformable gasket 196, thereby increasing the friction between piston assembly 154 and housing assembly 152. The increased friction caused by sliding piston assembly 154 forward relative to housing assembly 152 can be tailored to correspond generally with the increased restoring force caused by the increased deflection of steering section 32.

In similar fashion, translation of piston assembly 154 in a proximal direction (i.e. backward) relative to housing assembly 152 reduces the deflection steerable section 32 and the attendant restorative force exerted on pull wire 35. The frictional force generated by deformable gasket 196 is decreased by virtue of an increase in the radial distance between glide assembly 181 and piston guide 178 at deformable gasket 196. As such, translating piston assembly 154 to increase deflection of steering section 32 increases both the restorative force exerted by steering section 32 and the counteracting frictional force that counters the restorative force, while translating piston assembly 154 to reduce deflection of steering section 32 decreases both the restorative force and the counteracting frictional force.

According to an embodiment of the invention, central slider 176 and glide assemblies 181, 181a can each comprise interlocking threads such that central slider 176 and glide assemblies 181, 181a can be easily screwed together and separated. As such, either glide assembly 181 or 181a can separated from piston assembly 154 and replaced with an alternatively configured glide assembly 181 having a linear glide surface such as the parallel glide surface 187 and an angled glide surface 218 or a non linear glide surface. The modularity of glide assembly 181, 181a enables users to easily interchange glide assemblies 181 having different glide surfaces 218 to suit the user's preferences or the requirements of the particular medical procedure to be performed. Furthermore, glide assemblies 181, 181a can be manufactured by a machined process that produces glide assemblies 181, 181a inexpensively. Similarly, glide assembly 181 or 181a can be easily removed from central slider 176 to change the number of spacer gaskets 208, further increasing the modularity and customizability of control handle 150.

In assembly, central slider 176 is inserted into piston guide 178, and split pin 180 is fed through both access holes 215 of piston guide 178 and slot 186 of central slider 176. Catheter assembly 22, with pull wire 35 extending from proximal portion 24, is laid out with disassembled components including steering knob 174, distal portion 162, cavity 184 and the central slider 176/piston guide 178 combination. The proximal end of pull wire 35 is then threaded through these components and fed through pull wire notch 212 of split pin 180. Steering knob 174 is then fed through distal portion 162 and attached to central slider 176. Distal portion 162 of housing assembly 152 is threaded over the threaded exterior 192 of piston guide 178. Distal portion 162, now attached to piston guide 178, is axially positioned so that split pin 180 is at a desired position within slot 186 for the neutral position of steering section 32. Pull wire 35 is secured to split pin 180 by setting crimp 214 into split pin 180, which crimps pull wire 35 within split pin 180. Proximal portion 160 of housing assembly 152 can then be threaded over piston guide 178 and brought into contact with distal portion 162. The contact between proximal and distal portions 160 and 162 locks the housing assembly 152 in place.

In one embodiment, the clearance between access holes 215 and split pin 180 can affect a press fit on the unsplit end of split pin 180. Alternatively, split pin 180 can affect a looser, sliding fit initially, with the action of setting crimp 214 causing split pin 180 to be set within access holes 215.

Pull wire 35 may subsequently creep after being under tension for some time, creating slack or a dead band in the operation of the handle 150. Adjustment to eliminate the slack can be accomplished by breaking contact between proximal and distal portions 160 and 162 of housing assembly 152 (e.g., by turning back the proximal portion 160) and rotating distal portion 162 about piston guide 178 to adjust the position of the distal portion 162 relative to piston guide 178 and eliminate the slack. Proximal portion 160 is then brought back into contact with distal portion 162 to again lock the proximal and distal portions 160 and 162 together. Alternatively, the same procedure can be followed to relieve excessive tension in pull wire 35 when the catheter assembly 22 is in the neutral orientation.

Referring to FIG. 9, a force vs. handle displacement graph 240 of the forces of operation of various embodiments of the invention are presented. The abscissa of graph 240 presents the "handle displacement" 242, that is, the linear displacement of central slider 176 within housing assembly 152. The minimum of handle displacement 242 (FIGS. 6 and 6A) corresponds to substantially no tip deflection (origin of graph 240) and the maximum of handle displacement 242 corresponds to a maximum tip deflection (FIGS. 8 and 8A) at the maximum of the abscissa. The ordinate of graph 240 represents the force 244 exerted on the pull wire.

A restorative force curve 248 represents the actuation force exerted on the pull wire to further increase the displacement of central slider 176. A constant frictional force curve 250 represents the actuation force exerted on the pull wire to further increase the displacement of central slider 176 in the presence of a substantially constant frictional force exerted on central slider 176 by deformable gasket 196. A variable frictional force curve 252 represents the actuation force exerted on the pull wire to further increase the displacement of central slider 176 in the presence of a variable frictional force exerted on central slicer 176 by deformable gasket 196.

To hold steering section 32 at any given deflection, the frictional force must exceed the restorative force curve 248 at any given point on the abscissa of graph 240. Because a constant frictional force device exerts a fixed frictional force regardless of handle displacement 242, a constant frictional force 256 must exceed a maximum force 258 of the restorative force curve 248.

Figure 5:
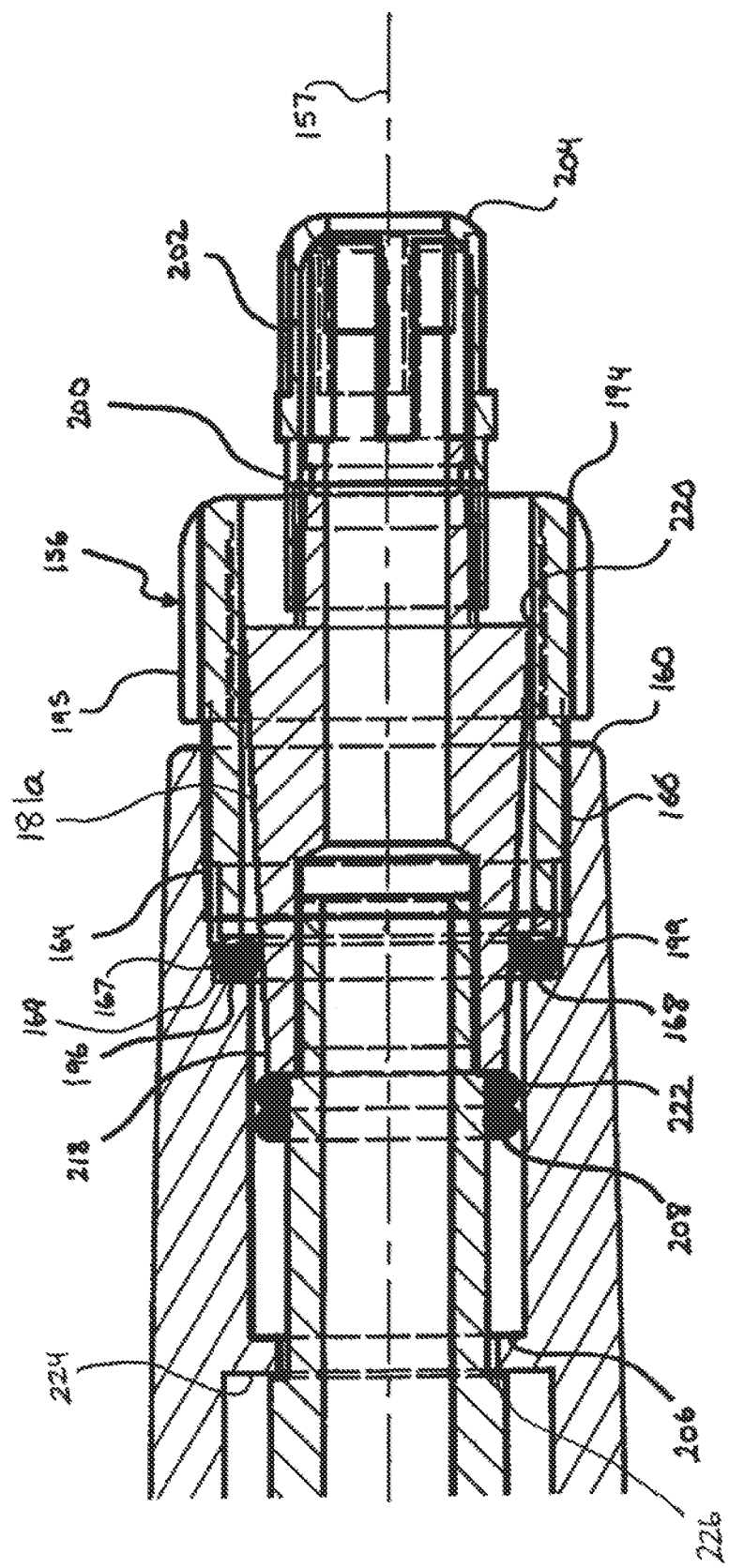
FIG. 5 is an enlarged partial sectional side view a control handle having an angled glide surface according to an embodiment of the invention.

However, with a variable frictional force device, such as depicted at FIG. 5, variable frictional force curve 252 can be tailored to exceed the restorative force locally along the abscissa of graph 240. This enables a variable frictional device to operate at lower actuation forces at lower handle displacement 242 (i.e. at lower tip deflections). The result is that driving the tip from no deflection to maximum deflection requires substantially less energy with the variable frictional device. An energy savings 260 that results is depicted by the cross-hatched area on the graph 240. The significance of reduced energy is lower operator fatigue over the course of a surgical procedure.

Figure 10:
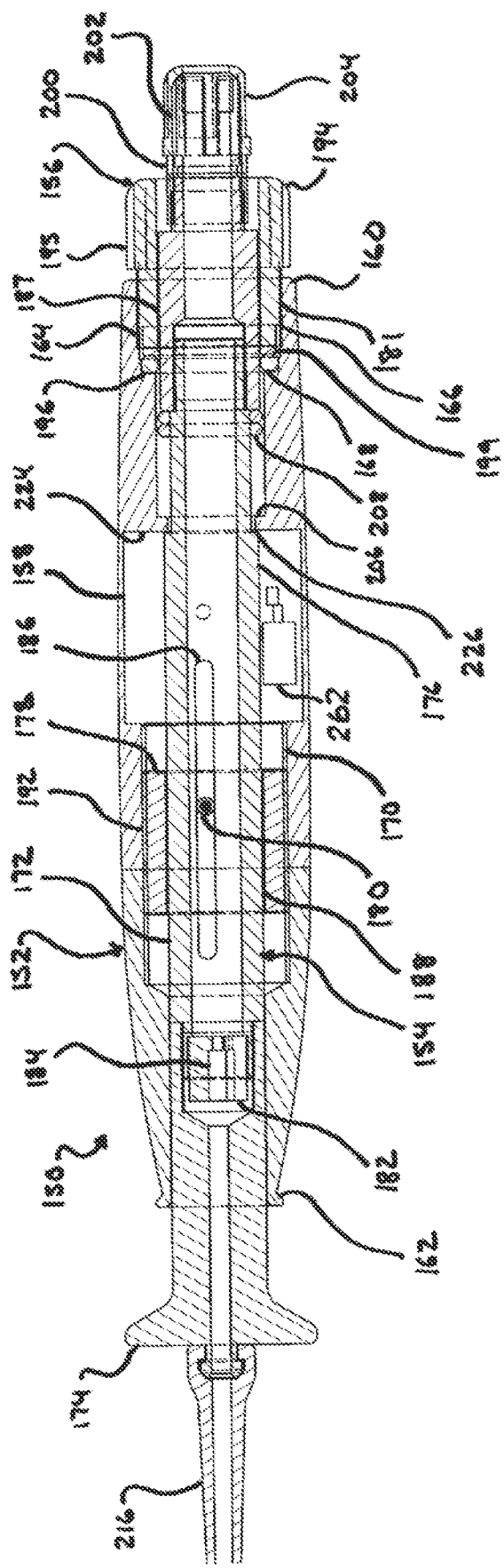
FIG. 10 is a sectional side view of a control handle with a vibrating motor.

Referring to FIG. 10, a vibrating motor 262 for inducing a vibration that can be sensed on housing assembly 152 is depicted in assembly with handle 150 according to an embodiment of the invention. Vibrating motor 262 can comprise a conventionally shaped vibrating motor such as the mini vibrating motor (DCM-382) or pancake shaped vibrating motor (DCM-373) available from All Electronics Corp. of Van Nuys, Calif., U.S.A. Vibrating motor 262 can be implemented as tactile feedback device 50 of FIG. 1 to provide a physical sensation with increasing amplitude and/or intensity to the user as the force applied to the catheter tip exceeds a predetermined "safe" threshold and increases above the threshold.

Figure 11A:
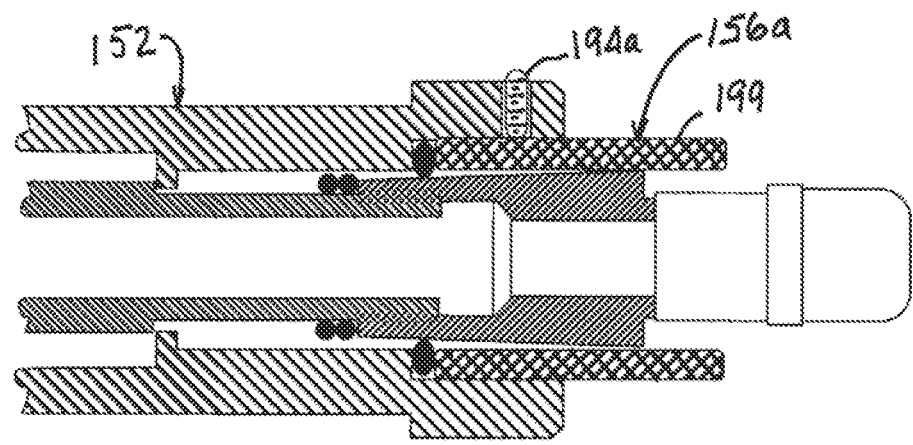
FIGS. 11A and 11B are sectional views of resistance adjusting assemblies in embodiments of the invention.
Figure 11B:
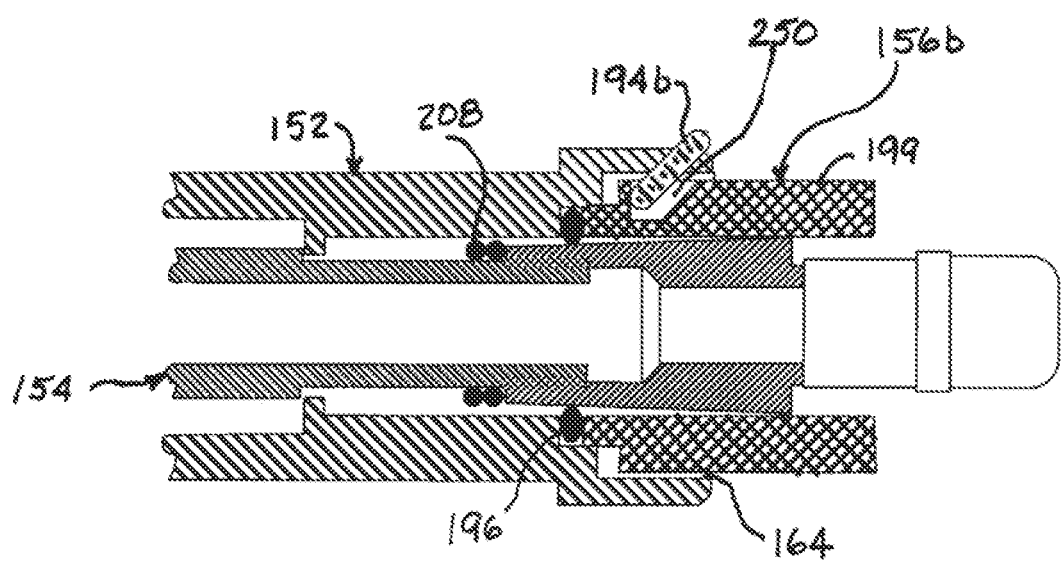

Referring to FIGS. 11A and 11B, alternative resistance varying assemblies 156a and 156b are presented in embodiments of the invention. In these configurations, threaded members 194a and 194b, respectively, can comprise set screws. For resistance varying assembly 156a, threaded member 194a is oriented to engage bushing 199 in a radial direction. To adjust the resistance of the control handle 150, bushing 199 is exerted against deformable gasket 196 to provide the desired resistance, then set in place using threaded member 194a. For resistance varying assembly 156b, threaded member 194b is oriented to engage bushing 199 in a canted direction (i.e. between a purely axial and a purely radial orientation).

To adjust the resistance of the control handle 150, threaded member 194b is adjusted to motivate bushing 199 to exert against deformable gasket 196 and provide the desired resistance. Threaded member 194b registers inside a notch or groove 250 to exert a force having an axial component on bushing 199. Threaded member 194b can be held in position using thread locking paste or by other ways known in the art.

While the invention is amenable to various modifications and alternative forms, specifics thereof have been shown by way of example only. It is understood that the intention of the foregoing descriptions and depictions are not to limit the invention to the particular embodiments described. To the contrary, the intention is to cover all modifications, equivalents, and alternatives falling within the spirit and scope of the invention as defined by the appended claims.

For purposes of interpreting the claims for the invention, it is expressly intended that the provisions of Section 112, sixth paragraph of 35 U.S.C. are not to be invoked unless the specific terms "means for" or "step for" are recited in the subject claim.

The invention claimed is:

1. A steerable catheter, comprising:
a catheter shaft;
a control handle coupled to the catheter shaft, the control handle comprising:
a housing assembly having a proximal portion and a distal portion and defining a central axis, wherein the proximal portion defines a central bore concentric with the central axis, the central bore including a radial step that defines a shoulder concentric about the central axis;
a deformable gasket disposed adjacent to the radial step; and
a tapered glide assembly disposed within the central bore of the housing assembly, the tapered glide assembly comprising a frustum which extends into and beyond the central bore of the housing assembly, the frustum defined by an angled glide surface extending along the entire longitudinal length of the frustum, wherein the angled glide surface is tapered radially inward from a proximal edge to a distal edge of the angled glide surface, and wherein the angled glide surface is in contact with the deformable gasket in the central bore of the housing assembly,
wherein translation of the tapered glide assembly in the distal direction causes a distal end of the catheter to deflect.

2. The steerable catheter of claim 1, wherein the angled glide surface is tapered radially inward from the proximal edge of the angled glide surface to the distal edge of the angled glide surface, such that an outer diameter of the tapered glide assembly is narrower at the distal edge than the proximal edge.

3. The steerable catheter of claim 2, wherein the translation of the tapered glide assembly in the distal direction further generates an increased frictional force between the deformable gasket and the angled glide surface.

4. The steerable catheter of claim 3, wherein the increased frictional force counteracts a restorative force of the catheter shaft, the restorative force being generated in response to the deflection of the catheter shaft.

5. The steerable catheter of claim 2, wherein the translation of the tapered glide assembly in a proximal direction generates a decreased frictional force between the deformable gasket and the angled glide surface.

6. The steerable catheter of claim 1, wherein the angled glide surface comprises a non-linear glide surface.

7. The steerable catheter of claim 1, further comprising a resistance adjusting assembly coupled to a distal end of the housing assembly, wherein the resistance adjusting assembly defines a bearing surface disposed at a distal end of the resistance adjusting assembly.

8. The steerable catheter of claim 7, wherein the bearing surface and the radial step define a gland in which the deformable gasket is disposed.

9. The steerable catheter of claim 8, wherein the resistance adjusting assembly is configured to move proximally and distally to adjust a size of the gland.

10. The steerable catheter of claim 9, wherein a friction between the deformable gasket and the angled glide surface is adjusted in response to the adjustment in the size of the gland.

11. A steerable catheter, comprising:
a catheter shaft;
a control handle coupled to the catheter shaft, the control handle comprising:
a housing assembly having a proximal portion and a distal portion and defining a central axis, wherein the proximal portion defines a central bore concentric with the central axis, the central bore including a radial step that defines a shoulder concentric about the central axis;
a resistance adjusting assembly coupled to a distal end of the housing assembly, wherein the resistance adjusting assembly defines a bearing surface disposed at a distal end of the resistance adjusting assembly, the radial step and the bearing surface defining a gland;
a deformable gasket disposed adjacent to the radial step; and
a tapered glide assembly disposed within the central bore of the housing assembly, the tapered glide assembly comprising a frustum which extends into and beyond the central bore of the housing assembly, the frustum defined by an angled glide surface extending along the entire longitudinal length of the frustum, wherein the angled glide surface is tapered radially inward from a proximal edge to a distal edge of the angled glide surface, and wherein the angled glide surface is in contact with the deformable gasket in the central bore of the housing assembly,
wherein translation of the tapered glide assembly in the distal direction causes a distal end of the catheter to deflect.

12. The steerable catheter of claim 11, further comprising structure that defines a port on a proximal end of the proximal portion of the housing assembly, the port being concentric with the central axis and extending proximal to the shoulder of the central bore, the resistance adjusting assembly being disposed in the port.

13. The steerable catheter of claim 12, wherein the port includes a threaded portion that engages the resistance adjusting assembly.

14. The steerable catheter of claim 13, wherein the bearing surface of the resistance adjusting assembly is defined by a bushing, the bushing being operatively coupled with the threaded portion.

15. A steerable catheter, comprising:
a catheter shaft;
a control handle coupled to the catheter shaft, the control handle comprising:
a housing assembly having a proximal portion and a distal portion and defining a central axis, wherein the proximal portion defines a central bore concentric with the central axis, the central bore including a radial step that defines a shoulder concentric about the central axis;
a deformable gasket disposed adjacent to the radial step; and
a tapered glide assembly disposed within the central bore of the housing assembly, the tapered glide assembly comprising a frustum which extends into and beyond the central bore of the housing assembly, the frustum defined by an angled glide surface extending along the entire longitudinal length of the frustum, wherein the angled glide surface is tapered radially inward from a proximal edge to a distal edge of the angled glide surface, and wherein the angled glide surface is in contact with the deformable gasket in the central bore of the housing assembly,
wherein translation of the tapered glide assembly in the distal direction generates an increased frictional force between the deformable gasket and the angled glide surface to cause a distal end of the catheter to deflect; and
wherein translation of the tapered glide assembly in a proximal direction generates a decreased frictional force between the deformable gasket and the angled glide surface to transition the distal end of the catheter from deflection to non-deflection.

16. The steerable catheter of claim 15, wherein translation of the tapered glide assembly in the distal direction increases a contact between the angled glide surface and the deformable gasket.

17. The steerable catheter of claim 15, wherein translation of the tapered glide assembly in the proximal direction decreases a contact between the angled glide surface and the deformable gasket.

18. The steerable catheter of claim 15, wherein the angled glide surface comprises a non-linear glide surface.

\* \* \* \* \*